United States Patent [19]

Douglas-Hamilton et al.

[11] Patent Number: 4,896,967

[45] Date of Patent: Jan. 30, 1990

[54] MOTILITY SCANNER AND METHOD

[75] Inventors: Diarmaid H. Douglas-Hamilton, Beverly; Paul Boisseau, Waltham, both of Mass.

[73] Assignee: Hamilton-Thorn Research, Danvers, Mass.

[21] Appl. No.: 167,682

[22] Filed: Mar. 11, 1988

Related U.S. Application Data

[63] Continuation-in-part of Ser. No. 897,036, Aug. 15, 1986.

[51] Int. Cl.$^4$ .................... G01N 21/59; G01N 21/45; G01N 33/487
[52] U.S. Cl. .................................. 356/442; 350/509; 350/523; 356/244; 382/6; 435/291
[58] Field of Search ............... 350/509, 523, 525, 526, 350/533, 536; 356/244, 442; 435/291

[56] References Cited

U.S. PATENT DOCUMENTS

| 4,407,569 | 10/1983 | Piller et al. | 350/509 |
| 4,690,678 | 9/1987 | Douglas-Hamilton | 604/349 |

OTHER PUBLICATIONS

Edmonds "Light-Emiting Diode Optical Probe For Epitaxial Film Characterization" IBM Tech. Disc. Bull. vol. 14 #9, Feb. 1972 pp. 2610-2611.
Wren "Understanding & Using The Phase Microscope" Unitron Educational Pub., pp. 32-36.
Bausch & Lomb Catalog D-104, pp. 5-7.
Unitron-Phase-Microscope MP-Series.
"Le System Sperdyn"-Mesurez L'Activite Des Spermatozoides by Gaclma, France.
Von F. Zernike "Das Phasenkontrastverfahren . . ." *Physik Zeitsch* XXXVI, 1935, pp. 848-851.
F. Zernike "Phase Contrast, A New Method for the Microscopic Observation of Transparent Objects," *Physica IX,* No. 7 (Jul. 1942) 686-698.
K. Yamamoto et al., "Some Improvements in the Phase Contrast Microscope", *Journal of Microscopy,* vol. 129, Pt. 1. Jan. 1983, pp. 49-62.

*Primary Examiner*—Vincent P. McGraw
*Attorney, Agent, or Firm*—Morse, Altman, Dacey & Benson

[57] ABSTRACT

An improved motility scanner is disclosed for characterizing the motion of sperm, bacteria, particles suspended in flowing fluids and the like. The motility scanner includes an improved optical system, a source of illumination for the system and radiation sensing means including electronic image reversal means coupled to the system. A disposable specimen holder allows external loading thereof and its positioning on a heated specimen support. The illumination source functions as a collimator in directing all of the emanating illumination onto the specimen. Both directly transmitted light and light scattered by the specimen are received by an imaging lens and are both focussed thereby onto pixels of a light sensitive device. A movable plate provided with a retarding member is designed to be located at the plane conjugate to the plane of the small source aperature. The directly transmitted light is transmitted through the retarding member and/or the attenuating member. The light scattered by the specimen, however, travels for the most part through the plate in areas not covered by the retarding and/or attenuating members.

8 Claims, 4 Drawing Sheets

MOTILITY SCANNER AND METHOD

This is a continuation-in-part of pending application Ser. No. 897,036 filed Aug. 15, 1986, entitled "Motility Scanner and Method."

BACKGROUND OF THE INVENTION

1. Field of the Invention

The present invention relates generally to the characterization of the motion of particles suspended in a liquid medium and, more particularly, to an improved device and a method developed for characterizing the motion of sperm, bacteria, particles suspended in flowing fluids, Brownian motion and the like.

2. The Prior Art

The characterization of the motion of particles suspended in a liquid medium is of particular significance in fertility analysis. The term "characterization" as used in this specification and in the appended claims is intended to define a procedure involving analyzing and determining the motion of particles in a liquid medium. Motility analysis as regards fertility includes the determination of sperm motility and mean sperm velocity. The term "sperm motility" is intended to to be defined as the fraction of sperm moving among all the sperms in a given specimen sample. The term "progressive motility" is intended to define the fraction of sperm moving in an approximately constant direction. The term "progressivity" or "linearity" is the ratio between the distance travelled and the track length.

Motility analysis is undertaken regularly for animals, such as horses, in particular race horses, and prime bulls, in order to establish and to keep a permanent running record of the quality of their semen, hence their breeding potential. Motility analysis also represents an important segment in diagnosing certain reproductive problems in the human male.

For the most part, sperm motility and mean sperm velocity are simply estimated by visual examination of a drop of semen on a slide. The results of such visual examinations vary widely, often by as much as 40%, from one observer to another. Further, one cannot estimate, purely on a visual examination, linearity or velocity distribution functions. In order to determine such linearity or velocity distribution functions, a method of multiple exposure time-lapse photography has been developed. This method is tedious and time consuming in that it requires the manual counting of the sperm tracks, followed by manual derivation of the distributions of linearity and velocity. In order to speed up this manual method, a computerized version thereof has been developed which allows for the calculation of the distribution functions, but only after the sperm tracks first have been manually outlined by using an interactive indicating device such as a light pen or a "mouse". A further improved version employs a microscope attached to a computer, video recorder and other peripheral items. This improved version is designed to analyze a drop of semen in a special cell, called the Makler cell. The Makler cell is such that it maintains an exact narrow spacing, usually 0.01 mm, between its opposed walls. Such an exact narrow spacing is required so as to provide a sharp focus for the microscope image, to reduce the visual density and thus enable the computation of sperm density. The narrow spacing of the Makler cell, however, constricts the motion of the sperm tails. Sperm tails are believed to require 0.02 to 0.10 mm diameter about their axes, depending on species, in order to operate and move freely, i.e., without constriction. Consequently, a system employing the narrow Makler-type cell spacing adversely affects the very quantities, e.g., motility, velocity and linearity, that it is designed to measure. Such system also makes it very difficult to measure the motion of sperm in a diluent since sperm density is reduced to such a degree that obtaining statistically significant numbers of sperm requires a long time, and the superposition of many successive fields. The measurement of sperm motion in a diluent is frequently required in motility analysis. For example, in in vitro fertilization experiments, the semen may be diluted by a factor of 100 to 500. Further, the Makler cell is expensive to make and, in use, is difficult to maintain at an exact, controllable temperature.

In said prior pending application Ser. No. 897,036 filed Aug. 15, 1986, we have disclosed a motility scanner in which only light scattered by and from the specimen is able to reach the optical system. More specifically, the design of the prior motility scanner is such as to assure that the imaging lens thereof receives no directly transmitted light. As a result, the image formed appears bright on a dark background, a dark field image. Two significant advantages derive therefrom. First, analysis of sperm motion is facilitated since only the important objects, the sperms, appear bright and the microprocessor system is easily programmed to consider only bright objects. Second, a considerable depth of focus can be obtained, allowing thereby the use of specimen holding chambers of a size in which the motion of the sperm cells is not constrained by the presence of walls. These advantages, albeit remaining significant, are nevertheless obtained at the cost of poorer image resolution. Consequently, sperm cell heads appear as extended spots, and the sperm cell tails are visible only, if at all, in rare circumstances. As a result, it is impossible to tell what portion of the non-moving objects represents detritus or non-motile sperm cells. In accordance with the present invention, the presence of a visible sperm cell tail resolves this problem. A sharper image resolution also causes the sperm cell heads to appear reduced in size of the total area covered by the sperm cell heads. This reduced area, in turn, decreases the probability of sperm cell head collisions, since the apparent cross-section is smaller. The proportion of tracking errors at a given sperm cell concentration is markedly reduced thereby. Further, accurate analysis at higher values of sperm cell concentrations also is now possible.

SUMMARY OF THE INVENTION

It is a principal object of the present invention to overcome the above disadvantages by providing an improved motility scanner for characterizing the motion of sperm, bacteria, particles suspended in flowing fluids and the like.

More specifically, it is an object of the present invention to provide an improved motility scanner for characterizing the motion of sperm, bacteria, particles suspended in flowing fluids and the like, comprising an improved optical system including an imaging lens; a source of illumination provided for the optical system; a heated specimen support disposed in the object plane of the imaging lens; a specimen holder, preferably disposable, designed to be positioned on the heated specimen support; radiation sensing means coupled to the optical system at the plane conjugate to the plane of the specimen; signal processing means, including electronic image reversal means, for analyzing the signals generated by the radiation sensing means; and display means connected to the signal processing means for displaying information characteristic of the motion of the sperm, bacteria, particles suspended in flowing fluids or the like. Preferably, the source of illumination comprises a single LED, combined with a small source aperture, functioning as a collimator directing its illumination onto the specimen in the specimen holder, with both the directly transmitted light and the light scattered by the specimen being admitted into the imaging lens. A movable plate, provided with a centrally disposed retarding member and/or attenuating member, is designed removably to be located in the beam of radiation of the imaging lens at a plane conjugate to the plane of the small source aperture. With the movable plate in the path of the beam, the directly transmitted light is transmitted through the retarding and/or attenuating member. The light scattered by the specimen however travels, for the most part, through the plate in areas not covered by the retarding and/or attenuating members. Preferably, the motility scanner also is contained within a portable or transportable housing. The motility scanner is provided with a transformer and a power cord whereby it can be connected to a conventional 115 V.A.C. power source. The improved motility scanner can be used in one of three operative modes: (a) with bright field illumination; (b) with dark field illumination; or (c) with phase contrast in dark field illumination.

Other objects of the present invention will in part be obvious and will in part appear hereinafter.

The invention accordingly comprises the motility scanner of the present disclosure, its components, parts and their interrelationships, the scope of which will be indicated in the appended claims.

Brief Description of the Drawings

For a fuller understanding of the nature and objects of the present invention, reference is to be made to the following detailed description, which is to be taken in connection with the accompanying drawings, wherein.

Detailed Description of the Preferred Embodiment

In general, the illustrated embodiment of a motility scanner 10, as depicted in schematic elevation and partly in section, is designed for the characterization of the motion of particles suspended in a liquid medium and has particular application to fertility analysis. In addition to motility analysis of sperm, the motility scanner 10 also is useful in analyzing and determining the motion of other items of interest, such as bacteria, particles suspended in flowing fluids, Browninan motion, and the like.

Figure 1:
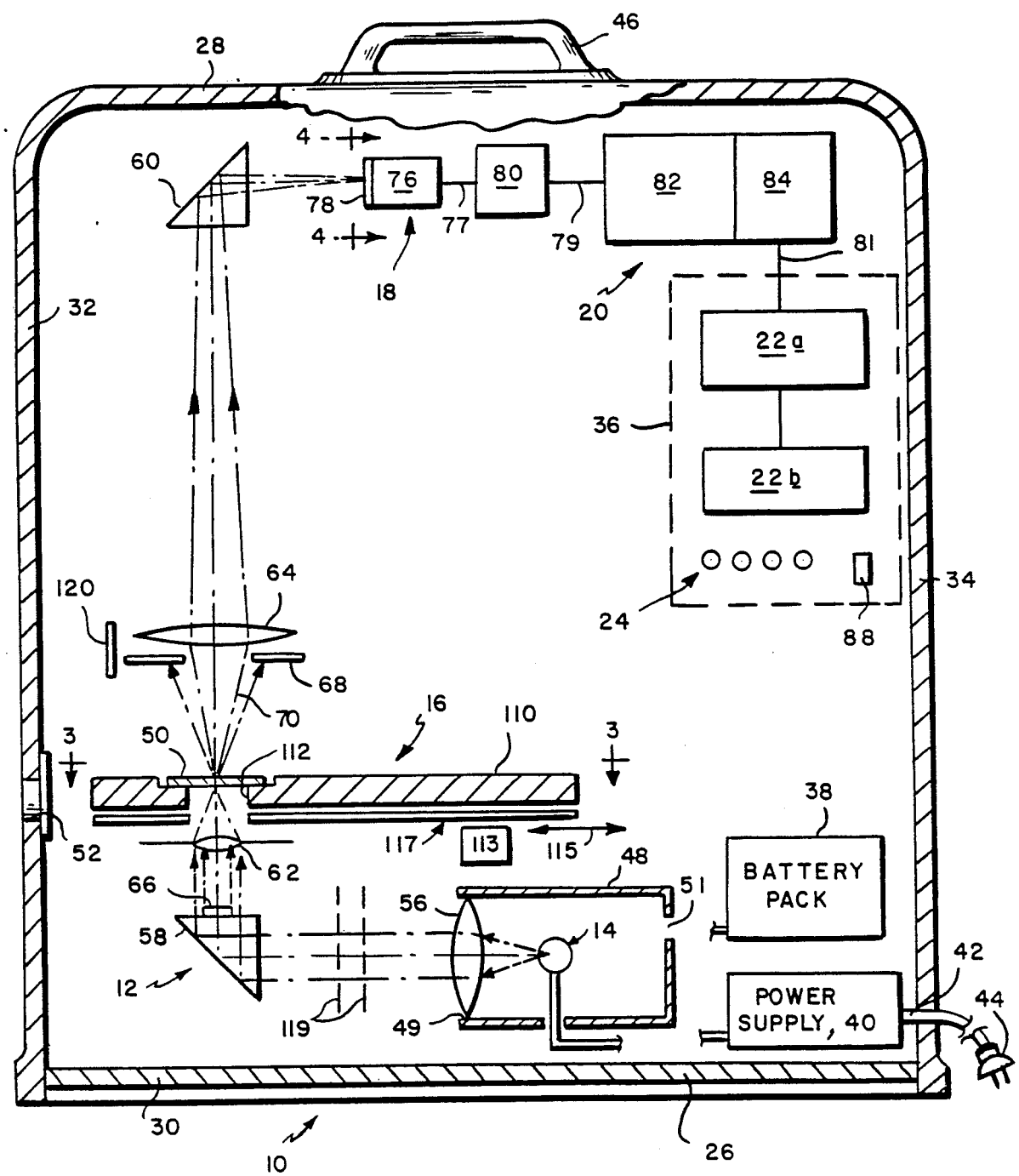
FIG. 1 is a schematic elevation, partly in section, of a motility scanner constructed in accordance with the invention.
Figure 7:
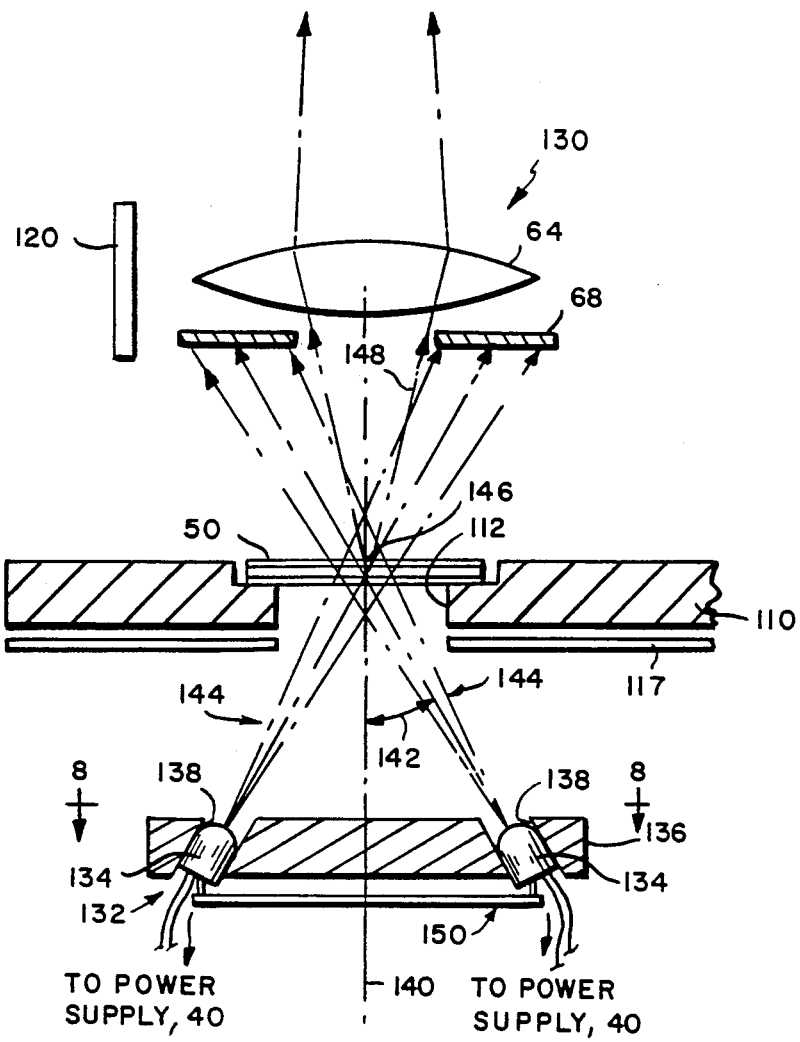
FIG. 7 is a partial view, similar to FIG. 1, but showing another embodiment of the motility scanner.
Figure 8:
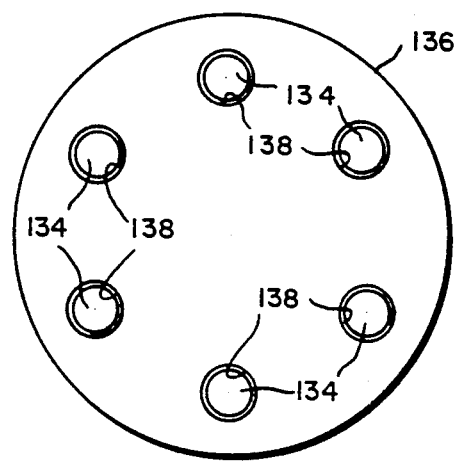
FIG. 8 is a plan view along the line 8—8 of FIG. 7.

The motility scanner 10, as illustrated in FIG. 1, essentially comprises an optical system 12, a source of illumination 14 for the optical system 12, a heated specimen support 16, radiation sensing means 18 coupled to the optical system 12, signal processing means 20 coupled to the radiation sensing means 18, display means 22 coupled to the signal processing means 20, and control means 24 for operating the motility scanner 10. Preferably, the motility scanner 10 is mounted within a portable housing 26, including a top wall 28, a bottom wall 30, and four side walls, two of which 32 and 34 are shown in FIG. 1. In the embodiment of FIGS. 7 and 8, the source of illumination comprises one or more LED's, as hereinbelow more fully described.

Preferably, the display means 22 and the control means 24 are located on a panel 36 set into the front side wall, not shown. The motility scanner 10 also preferably includes a power supply 40 and a power cord 42, having a plug 44, connected thereto. The source of illumination 14 preferably is connected in parallel to both the battery pack 38 and the transformer 40. It is to be understood that whenever the plug 44 is plugged into a conventional power outlet of 115 V.A.C., the internal battery pack 38 is automatically disconnected from also supplying power to the illumination source 14 and will remain so disconnected as long as the plug 44 remains plugged into the conventional power outlet. A convenient handle 46 is secured to the top wall 28, centrally thereof.

A specimen to be characterized by the motility scanner 10 is externally loaded into a specimen holder 50, which is then placed on a motorized and heated specimen support 16. The heated specimen support 16 slides through a slot 52 formed in the side wall 32, thereby retracting to position the specimen at the imaging point.

The Optical System of FIG. 1

The optical system 12 of the motility scanner 10 comprises a collimating lens 56, a condensing lens 62 and an imaging lens 64. A pair of reflecting elements 58 and 60 may be included to fold the light path. Preferably, the reflecting element 58 comprises a fully reflecting prism, as shown, and the reflecting element 60 comprises a front surface mirror. If desired, the element 58 also can be a mirror, or the like. It will be noted that the specimen support 16 and, more precisely, the thereon disposed specimen holder 50, are mounted at or near the focal plane of the condensing lens 62.

A focussing means 120 is operatively coupled to the imaging lens 64 to allow for the variation in the distance between the lens 64 and the specimen support 16. Also preferably one or more optical filters 119 are positioned between the collimating lens 56 and the reflecting element 58. These filters 119 are intended to remove unwanted spectral portions of the radiation emitted by the source 14.

The specimen holder 50 also is positioned during analysis at the object plane of the imaging lens 64, with the radiation sensing means 18 being disposed at the imaging plane of the imaging lens 64. An obscuring member 66, which preferably is a disk, is positioned on the exit side of the prism 58. It is to be understood that, in the alternative, the obscuring member 66 also can be bonded directly to the exit or entry sides of the prism 58. The function of the obscuring member 66, in cooperation with an aperture 68, is to assure that the imaging lens 64 receives no directly transmitted light. In the preferred embodiment, the condensing lens 62 produces an image of the obscuring member 66 on the aperture 68. Therefore, the imaging lens 64 accepts only light scattered or refracted into a cone of acceptance 70 by the specimen contained within the specimen holder 50. Consequently, any object present in the specimen which scatters or refracts light, such as a spermatozoon, will appear bright on a black background.

The imaging lens 64 is a single compound lens having an effective depth of field at its object plane of at least about 0.2 mm, and preferably about 0.5 mm, the significance of which will become apparent below. The focal length of the imaging lens can vary between about 2.5 cm to about 5 cm, with the latter being preferred. The magnification ratio of the imaging lens 64 preferably is less than ten-to-one and, typically is about four-to-one. The imaging lens 64, for example, can be a "Schneider Componon" enlarger lens made by the Schneider Kreuznach company in Germany.

The Radiation Sensing Means

Figure 4:
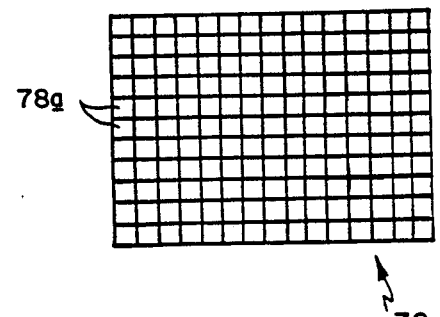
FIG. 4 is a view, on an enlarged sale and along the line 4—4 of another part of the motility scanner shown in FIG. 1.
Figure 5:
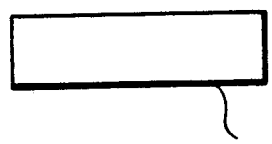
FIG. 5 is a plan view of an alternate specimen holder.
Figure 6:
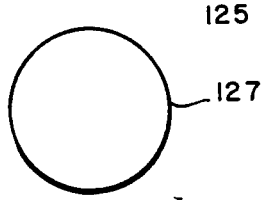
FIG. 6 is a plan view of still another specimen holder.

The radiation sensing means 18 of the motility scanner 10 preferably includes a light-sensitive device 76 provided with a plurality of light-sensitive cells 78, known as pixels, observe FIG. 4. The device 76, preferably a charge coupled device (CCD) or the like, generates an analog signal representative of the focused image on the pixels 78a of the device 78. Each pixel 78a is about 0.01 mm to about 0.02 mm in width. Since a typical sperm cell head has a diameter from about 0.002 mm to about 0.005 mm, one sperm cell head can be imaged on several pixels, using magnification 4 to 10. Further, each pixel 78a is designed so as to be able to discriminate, with uniform and stable sensitivity, up to sixty-four distinct levels of optical illumination intensity. Thus, light-scattering particles found in the specimen under investigation, such as spermatozoa, will appear bright in a dark field.

The analog signal representative of the focused image on the pixels 78 is transmitted via lead 77 to an analog to digital converter 80, also known as a frame grabber board, where the signal is converted to digital form on lead 79, and stored in RAM, preferably a 64 KByte RAM, from which it is available to the signal processing means 20. The signal processing means 20 essentially comprises a microprocessor 82 and a pre-programmed device 84. The microprocessor 82 preferably is capable of accessing in excess of a 1.5 MByte RAM included in the system, while the device 84 contains a plurality of pre-programmed read-only memory (ROM) chips. The output of the signal processing means 20 is transmitted via lead 81 to the display means 22. Display means 22 basically includes a screen 22a and a printer 22b. The screen 22a is a typical CRT. In one form it is black and white. In other forms it can display colorcombinations and/or information in both graphical and alphanumeric form. The printer 22b preferably is a hard copy printer designed to reproduce the information appearing on the screen 22a on paper upon command of the operator, effected by depressing one of the control buttons of the control means 24. In one embodiment, the printer is an integral part of the motility scanner. In another embodiment it is an external peripheral. A power switch 88 allows the motility scanner 10 to be rendered operational.

The Specimen Holder

Figure 2:
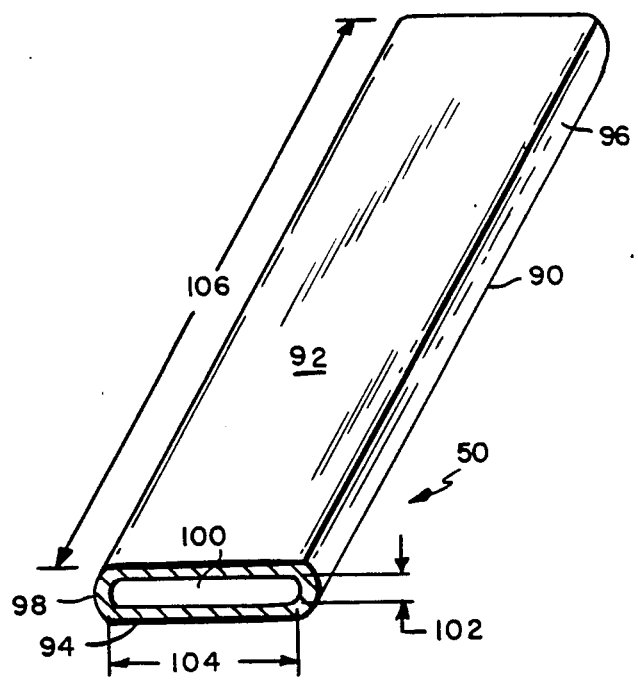
FIG. 2 is an isometric perspective view, on an enlarged scale, of a part of the motility scanner shown in FIG. 1.
Figure 3:
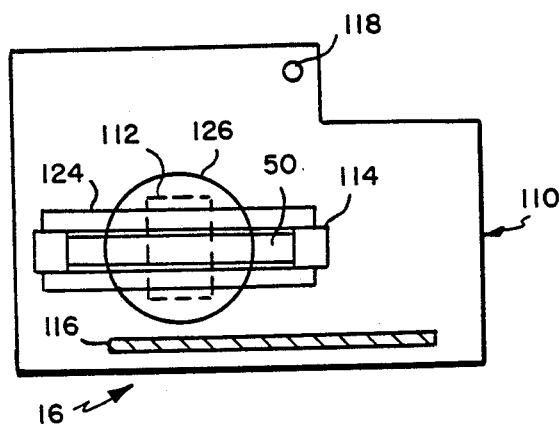
FIG. 3 is a plan view, along the line 3—3, of a portion of the motility scanner of FIG. 1.

The specimen holder 50 for the motility scanner 10 is shown, in isometric perspective and on an enlarged scale, in FIG. 2, and its operative use is illustrated in FIG. 3. As noted, the specimen holder 50 comprises a flat tubular member 90 formed of a hard, transparent material, such as glass or plastic, with a pair of adjacently spaced wide parallel sides 92 and 94 and remotely spaced short, curved connecting sides 96 and 98, cooperately defining therebetween a specimen holding channel 100. Preferably, the specimen holding channel 100, which is open at its respective ends, is formed with a depth 102 of about 0.2 mm between its wide parallel sides 92 and 94, a width 104 of about 2 mm between its curved connecting sides 96 and 98, and an axial length 106 of about 5 cm between its respective open ends.

The operative use of the specimen holder 50 is best described with reference to FIGS. 1 and 3. After the specimen holding channel 100 of the specimen holder 50 has been filled with a properly diluted sample, as more fully described below, the specimen holder 50 is placed on the retractable heated specimen support 16, which slides through the slot 52 in the side wall 32. Specimen support 16 includes a flat member 110, provided with a window 112 and a longitudinal slot 114. Member 110 is designed to slide in and out of the slot 52, as indicated by an arrow 115, with the aid of means 117. Means 117 preferably is a motorized means and slides with the aid of a small electric motor 113. Member 110 preferably is heated via an electrical resistance wire 116 embedded therein. Member 110 also is provided with a further and wider slot 124 designed to accomodate a microscope slide 125, if that is chosen to contain the specimen. In addition, member 110 also has a circular slot 126 designed to accomodate a Makler-type cell 127, if that is chosen to contain the specimen. It should be noted that each of these slots 114, 124 and 16 is so located as to center the respective specimen holder over the window 112.

When the microscope slide 125 is used to hold the specimen, the density of the sperm population therein is not known since the spacing between the slide 125 and its coverslip is not known. A user of the motility scanner 10 would find the employment of the Makler-type cell 127 particularly useful whenever more concentrated sperm dilutions were to be examined.

It should also be noted that the source of illumination 14 is completely enveloped, save for an opening 49 for the collimating lens 56, and an air cooling aperture 51, in a suitable enclosure 48.

The Embodiment of FIGS. 7 and 8

In the embodiment illustrated in FIGS. 7 and 8, a simplified optical system 130 is employed in the motility scanner due to a different source of illumination 132 used. This source of illumination 132 comprises at least one, and preferably more LED's 134, mounted in a ring-like manner in a support member 136. The support member 136 is provided with a plurality of apertures 138 to accomodate the LED's 134. Each of these apertures 138 is formed at an angle 142, inclined with respect to a central axis 140 of the member 136. The LED's are then mounted in the apertures 138 at this inclined angle 142, which is the angle between the maximum emission of radiation from the LED's 134 and the axis 140. This angle of convergence 142 can range from about 15° to about 45°, and preferably is about 25°. Variation in the angle of convergence 142 will either enhance or or weaken the motility scanner's ability to detect sperm rotation within the specimen holder 50. This is so since sperm rotation causes the sperm cell's image to increase or to decrease in intensity. The amplitude of this intensity change is related to the angle of incidence of the illumination on the sperm cell within the specimen holder 50.

Each LED 134 produces an intense, concentrated beam of forward directed radiation 144 directed at a point 146 of intersection of the specimen holder 50 and the central axis 140. Since each LED 134 independently illuminates the whole field of investigative interest of the specimen holder 50, one such LED 134 can suffice. In order to enhance the uniformity of illumination at the specimen holder 50, however, it is preferred that a ring of LED's 134 be employed. The number of LED's in the ring can vary anywhere from three to about twelve, with a ring of six LED's being preferred, as illustrated in FIG. 8. The geometry of the ring of LED's 134 is so designed as to prevent direct radiation from the LED's 134 from reaching and entering the imaging lens 64. Thus, the only radiation to reach and enter the imaging lens 64 is radiation within a cone of acceptance 148, which is radiation scattered by the particles within the specimen holder 50 whose motion the motility scanner is designed to characterize. These particles will, therefore, appear bright in a dark background.

Although any type of LED's can be used in the structure described with reference to FIG. 7, LED's emitting radiation in the infrared region are preferred. This is so since radiation in the infrared range, and particularly about and near 880 nanometers, propagates well through the optical glass frequently employed for making the specimen holder 50 and the optical train. Further, the sensitivity of the CCD detector 76 at and near 880 nm is high, yielding a clear image, with adequate brightness. Still further, by using the longer wavelengths of illuminating radiation about and near 880 nm, we find that these longer wavelengths are less subject to scattering by smaller particles suspended in the diluent medium, whose presence otherwise might adversely affect the output results of the motility scanner. For example, when using a typical milk-based diluent medium for sperm analysis, one of the problems frequently encountered consists in the milk particles obscuring the optical transmission through the specimen holder 50 and in increasing the amount of scattering by such milk particles. As a consequence, the definition with which sperm cells normally can be discerned is markedly reduced. By using IR radiation, the scattering from the sperm tails also is reduced, enhancing thereby the characterization of sperm head movement. Unwanted scattering of infrared radiation, when compared to visible light, is greatly reduced, and consequently the image quality obtained is improved. At present, we prefer to use IR radiation emitting LED's, with an intensity half angle of 8° and having a peak emission at or near 883 nm, such as the GaAlAs LED's. Further, we prefer to operate these LED's at about 50% to about 75% power levels only so as to markedly increase their operational lifetimes.

It will be observed that in the structure of FIGS. 7 and 8 employing the LED's 134, as above described, in addition to the enhanced optical efficiency gained at a reduced generated heat (only about 2 watts heat as contrasted with about six times as much heat generated by a conventional hot filament lamp), both the collimating lens 56 and the condensing lens 62 are omitted, together with the prism 58 and the thereon placed obscuring member 66.

The Embodiment of FIGS. 9–13

In the embodiment illustrated in FIGS. 9–13, an improved optical system 160 is employed in the motility scanner of the invention. The improved optical system 160 excels at increased image resolution. As a consequence, non-moving objects appearing in the specimen under investigation can now be differentiated as non-motile sperm cells from detritus. Further, the improved optical system 160 allows for a marked reduction in the proportion of tracking errors at a given sperm cell concentration. The improved optical system 160 also allows for a more accurate analysis at higher values of sperm cell concentrations.

The improved optical system 160 essentially comprises a single LED illumination source 162 combined with a small source aperture 164 formed in a suitable enclosure 166 for the source 162. By using a single LED as the illumination source 162, the combination functions as a collimator. As such, it takes the place of both the collimating lens 56 and the condensing lens 62 of the optical system 12 illustrated in FIG.1. Similar collimating and condensing lenses also are required in conventional phase contrast systems. See specifically the article "Some improvements in the phase contrast microscope," by K. Yamamoto et al, *Journal of Microscope*, Vol. 129, Pt.1, January 1983, pp. 49–62, at p. 50. See also, F. Zernike, "Das Phasenkontrastverfahren bei der mikroskopischen Beobachtung," *Physik*, Z. XXXVI, 1935; and F. Zernike, "Phase Contrast, A New Method for the Microscopic Observation of Transparent Objects," *Physica IX*, No. 7, July 1942, pp. 686–698. Preferably, the single LED is a super-bright LED with a high level of intensity, as represented by an LED, Type No. H-2000, operable at a peak wavelength of 660 nm, with a half-angle spread of 5°, as made by the Stanley Electric Co., Ltd. of Japan. Other equally or more powerful LED's; and other, shorter wavelengths, also can be employed.

Unlike both of the system of FIG.1 herein and the phase contrast system employed in microscopes, in the improved optical system 160 of the present invention, all of the illumination emanating as beam 168 from the single LED source 162, as collimated by the precisely positioned small source aperture 164, is directed at the specimen contained within the specimen holder 50 supported on member 110. A part 170 of the beam 168 represents light transmitted through the specimen, while a part 172 is scattered by the specimen. Thus, both the directly transmitted light 170 as well as the light scattered 172 by the specimen are directed by a first reflecting element 174 at an imaging lens 176. The imaging lens 176, in turn, focuses both parts 170 and 172 of the beam 168 onto the light sensitive cells 78 of the light sensitive device 76 of the radiation sensing means 18, with the aid of a second reflecting element 178. Both parts 170 and 172 of the beam 168 recombine upon reaching the device 76 to form the image at the screen 22a, see FIG. 1. The resultant image is now presented in the bright field illumination mode, where the sperm cells appear as dark images on a relatively bright background.

Figure 9:
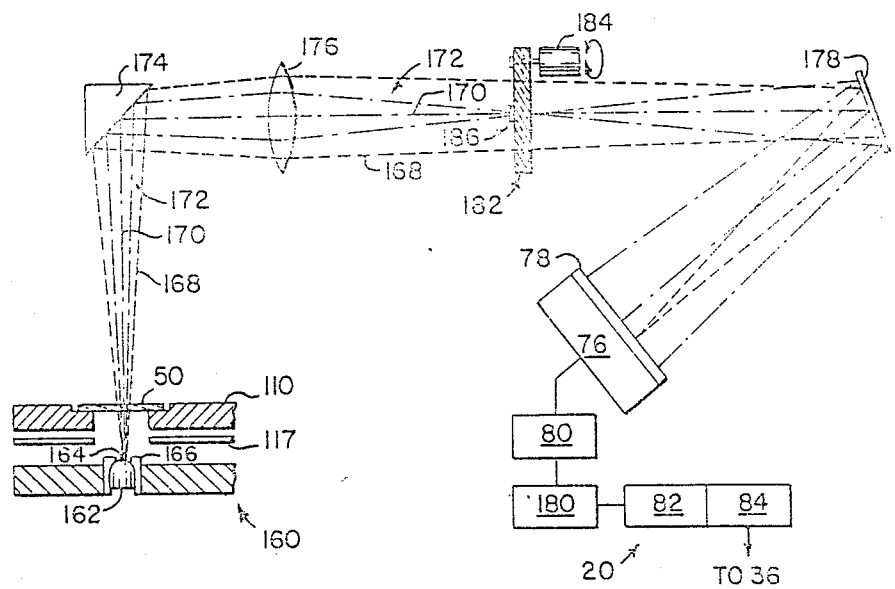
FIG. 9 is a partial view, similar to FIG. 1, but showing an improved optical system for the motility scanner of the present invention.

The improved motility scanner according to FIG. 9 also can be operated in a dark field illumination mode by incorporating an electronic image reversal means 180 in the radiation sensing means 18, preferably in the signal processing means 20. The image is inverted before analysis. With the aid of the electronic image reversal means 180, the image is electronically reversed, before being analysed by the microprocessor 82, into an image in which the sperm cells appear as bright images on a relatively dark background.

The improved motility scanner according to FIG. 9 also can be operated as a negative phase contrast system, resulting in heightened image resolution. Phase contrast is characterized by bright, bold illumination, but gives a dark field image. Phase retardation of the beam 168 is introduced into the system 160 by providing a specially designed plate 182 at the plane conjugate to the plane of the small source aperture 164 of the LED illumination source 162. At this conjugate plane, an image of the source aperture 164 is formed, the diameter of which image is the diameter of the source aperture 164 multiplied by the magnification ratio of the optical system 160. The plate 182 is designed to be moved between a first operative position within the beam 168, illustrated in solid lines, to a second operative position, shown in phantom lines, outside of the beam 168, by an appropriately designed holder 184. Preferably, the motion is a rotating one, swinging the plate 182 in or out of the beam 168, as desired by the user. The plate 182 is provided with a centrally disposed coating 186 of a retarding member 188 and/or an attenuating member 190, as more fully described below with reference to FIGS. 10-13. As will be observed in FIG. 9, the part 170 of the beam 168 representing the directly transmitted light travels through this centrally disposed coating 186. On the other hand, the part 172 of the beam 168 representing the light scattered by the specimen in the specimen holder 50, for the most part, travels through the plate 182 outside of the centrally disposed coating 186, the significance of which will be more fully described below.

Figures 10, 11, 12, 13:
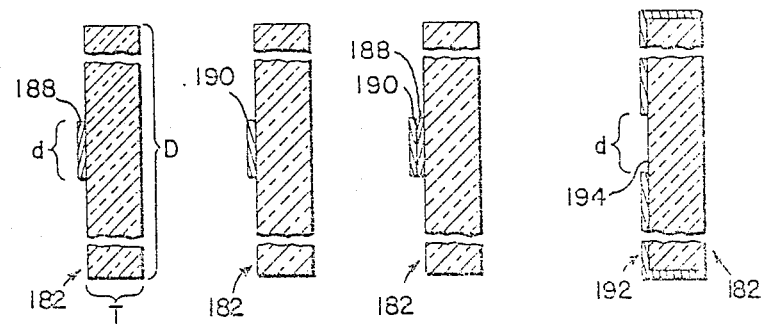
FIGS. 10 through 13 illustrate a part of the improved optical system of FIG. 9.

Preferably, the plate 182 comprises a disk formed of an optical glass window, with a preferred diameter (D) of about 25 mm and a preferred thickness (T) of about 3 mm, see FIG. 10. The centrally disposed coating 186 preferably is provided thereon by evaporation, using a specially designed and constructed mask 192, observe FIG. 13. The mask 192 is so designed and constructed as to securely hold and mask the plate 182 during the evaporation process, except for a central spot 194 with a diameter (d), the desired diameter for the coating 186. With a preferred diameter for the coating 186 of about 0.115 inch and a magnification ratio of 2.875 for the optical system 160, a small source aperture 164 of about 0.04 inch diameter is called for. It is understood that varying the size of one will affect the size of the remaining two variables, according to the relation expressed above.

As stated, the coating 186 comprises either the phase retarding member 188, illustrated in FIG. 10, the attenuating member 190 illustrated in FIG. 11, or a combination of the retarding member 188 onto which the attenuating member 190 is deposited, preferably also by evaporation. Preferably, the retarding member 188 is formed with a thickness of about 120 nanometers and of a group including magnesium fluoride and titanium dioxide. Preferably, the attenuating member 190 also is formed from a nickel-base alloy characterized by high temperature oxidation resistance, such as Inconel alloy 600. Preferably, the attenuating member 190 provides an attenuation of the part 170 of the beam 168 transmitted therethrough of about 97%, transmitting only the remainder of about 3% of this part 170 of the beam 168.

With the plate 182 positioned by the holder 184 into the beam 168 of the imaging lens 176, the phase retarding member 188 of the coating 186 will retard the phase of the entire part 170, representing the directly transmitted light, of the beam 168 by one quarter wavelength. The part 172 of the beam 168, representing the light scattered by the specimen however, travels through the plate 182 for the most part outside of the reach of the phase retarding member 188 and is, therefore, not retarded. As a consequence, a sharp image is created in which even the tails of the sperm cells are clearly visible. And if the coating 186 also includes the attenuating member 190 superimposed on the phase retarding member 188, the contrast of the phase-contrast image is further increased, making analysis of the image of the sample specimen even more accurate. For here again, the part 172 of the beam 168 representing the light scattered by the specimen, in traveling through the plate 182 for the most part outside of the coating 186, is thus neither attenuated nor retarded relative to the directly transmitted part 170 of the beam 168. As mentioned, both parts 170 and 172 of the beam 168 recombine at the light sensitive device 76 of the radiation sensing means 18 to form the image projected onto the screen 22a of the motility scanner of the invention. The result is an image with a sharply improved optical resolution.

The improved optical system 160 further excels in being very stable against dislocation of the component parts during transport or installation. This is so since the system 160 is relatively tolerant of line-up errors.

Effecting a selection among the three modes of operation (bright field, dark field, and negative phase contrast) is easily done by manipulating one of the controls of the control means 24 located on the front panel 36 of the instrument. The phase contrast plate holder 184 can also be moved manually into or out of the beam.

The Preferred Process of the Invention

The preferred process of employing the motility detector 10 of the invention for characterizing the motion of sperm, bacteria, particles suspended in flowing fluids and the like will be illustrated with specific reference to equine semen, specifically that of stallions.

Note however that this does not preclude the use of a Makler chamber or specimen holder for more concentrated specimens. In using the phase-contrast optical system described in the embodiment of FIGS. 9-12, a Makler chamber (or Petroff-Hauser chamber) is indicated. This is because the depth of focus is greatly reduced in the use of phase-contrast optics, and therefore the specimen should be maintained within a 20 micron thickness. It should be pointed out, however, that phase contrast can still be used with the specimen holding chamber 100 described here. But the image of entire volume of chamber 100 cannot be focused simultaneously with phase-contrast optics onto the sensitive means 78. It is only possible to focus the cells swimming along the upper or lower walls of the chamber 100 when phase contrast optics is used.

A specimen sample, i.e., a drop of semen obtained from a stallion, is preferably first diluted with a suitable diluent and in a predetermined ratio. A suitable diluent is Hepes transparent extender or Kenney's (powdered milk and glucose) equine extender. The predetermined ratio of diluent to sample for stallions is in the range of about 50:1 to about 250:1, and preferably is about 250:1. The diluted sample is drawn up by capillary action into the specimen holding channel 100 of a specimen holder 50, one end of which is immersed below the surface of the diluted semen. The specimen holder 50 containing the diluted sample specimen is then placed on the heated specimen support 16, which is then moved back through the slot 52 into the motility scanner 10. As mentioned, the dimensions of the specimen holder 50 are such that it will slide within the channel guide 114 so that a portion of the specimen holder 50 will lie over the window 112 formed in the flat member 110, observe FIG. 3.

With the motility scanner 10 having been activated by turning the power switch 88 on, the flat member 110, preferably made of a thermally conductive material, such as aluminum, is maintained at a temperature of about 37° C. by an embedded resistor 116, through which an electric current is passed. A thermal sensor 118 also is embedded in the member 110 and is used to control the current passing through the resistor 116, and thereby its temperature. The temperature can be set using the control means 24. Member 110 is in turn maintaining the diluted sample within the specimen holder 50 at about the same temperature, i.e., about or slightly above normal body temperature. Due to this temperature and the dilution of the sample in the specified ratio, a milieu for the analyzed sample is being maintained throughout the process of the invention, which milieu most closely resembles that environment through which the sperm migrate normally and naturally. By depressing one of the control buttons of the control means 24, the source of illumination 14 and the signal processing means 20 are actuated and analysis of the specimen sample is effected. Focussing means 120 is provided to vary the distance between the imaging lens 64 and the specimen holder 50, producing thereby a sharp image at the image plane.

Since the effective depth of field of the imaging lens 64 at its object plane, precisely where the specimen holder 50 is disposed, exceeds the depth 102 of the specimen holder 50, the entire specimen depth is sharply imaged on the light-sensitive cells 78 of the charge coupled device 76. Further, since the imaging lens 64 is designed to maximize the modulation transfer function across a wide angular field, a high edge resolution of sperm in the analyzed sample is obtained. Sperm within the sample specimen now appear as bright objects on a black background. Successive images produced on the light sensitive cells 78, being representative of the sperm moving through the diluted sample, are then transmitted to the frame grabber board typically at about five frames per second, although higher or lower rates of image acquisition also can be used. These transmitted images are now stored in the RAM thereof. After a plurality of images have been so stored in the RAM, namely at least about 5 and preferably about 20 to 30 stored images, the image taking process ceases and analysis of the stored images commences.

A frame subtraction procedure first is employed which removes all stationary objects, caused by the presence of dirt or the like either in the optical system 12 or within the specimen sample, from the process so that only the moving parts, e.g., liver sperm, of the specimen sample are dealt with by the system. A background frame is constructed from at least one, typically three, of the recorded video frames, by comparing these video frames and retaining, pixel by pixel, the minimum of the three pixel values. The background frame constructed in this way is subtracted pixel by pixel, from each of the recorded vodeo frames. The resulting video images contain only the non-static component of the original images.

Following the removal of stationary objects from adversely affecting the process of motion characterization, analysis of the transmitted frames is then effected in and by the coded device 84, specifically by the plurality of ROM chips contained in the device 84. These ROM chips have previously been pre-programmed with instructions to analyse the transferred images from the light-sensitive cells 78 of the device 76 and to derive sperm velocity and linearity distribution functions therefrom. The motion characterization process includes analysis of the sperm tracks in which the velocity along the sperm track and the velocity between track end points are calculated, and the track linearity is derived as the ratio of the distance between the starting and the end points of the tracks to the total track length. Mean values of velocity and linearity are then computed and these averages, as well as the distributions of number of sperm versus velocity and linearity are displayed on the screen 22a and, if desired, printed on a hard copy by the printer 22b. Alternately, the tracks may be plotted on a plotter peripheral device. A typical screen display and/or information appearing on a copy from the printer 22b is illustrated in Example I.

| Example I | |
| --- | --- |
| DATA SUMMARY: | (time and date) |
| TOTAL OBJECTS | 50 million/ml. (185) |
| MOTILE OBJECTS | 23 million/ml. (88) |
| MOTILE/TOTAL | 47.6 percent |
| AVERAGE VELOCITY | 32.5 microns/second |
| AVERAGE P-VELOCITY | 24.1 microns/second |
| AVERAGE PROGRESS | 73.4 percent |
| PROGRESSIVITY DISTRIBUTION (PERCENT) | |
| 00–10 | 0 |
| 10–20 | 0 |
| 20–30 | ****** 2 |
| 30–40 | ***************** 8 |
| 40–50 | ******** 3 |
| 50–60 | ************************ 12 |
| 60–70 | ******************************************* 21 |
| 70–80 | ******************************************* 21 |
| 80–90 | ********************************* 16 |
| 90–100 | *************** 5 |
| VELOCITY DISTRUBITION (MICRONS/SEC) | |
| 00–10 | ** 1 |
| 10–20 | *************** 8 |
| 20–30 | ******************************************** 27 |
| 30–40 | ********************************************** 29 |
| 40–50 | ********************************* 19 |
| 50–60 | ******* 3 |
| 60–70 | ** 1 |
| 70–80 | 0 |
| 80–90 | 0 |
| 90–100 | 0 |

Computer counting of sperm tracks then yields an accurate determination of live sperm density, since the total volume of specimen examined is known exactly from the optical magnification and the internal wall separation of the specimen holder 50. In order to estimate the total sperm density, the dead sperm cells are identified by selecting all background (non moving) objects whose optical brightness and linear dimensions fall within certain limits. These limits are defined as multiples of the mean values determined for all the moving cells. In this way, use of an absolute illumination calibration can be avoided. The motility is then determined as the ratio of the number of mobile objects to the total number of objects falling within the above limits in the field.

Utilization of the motility scanner 10, together with the specimen holder 50, thus allows for accurate motion measurements of particles suspended in a fluid because:

(a) the particles enjoy complete freedom of motion without being constricted by walls;

(b) the design of the specimen holder 50 allows ample time for effecting the motion characterization of the specimen sample before any danger of the sample drying out;

(c) the optical system 12 allows for all of the spermatozoa or other moving particles contained within the specimen sample within the specimen holder 50 to be kept in clear focus throughout their movement within the depth 102 of the specimen holding channel 100;

(d) the known wall spacing of the specimen holder 50 allows exact determination of the volume, hence the density, of the sample; and (e) the geometry of the specimen holder 50 minimizes problems of mass fluid flows which might otherwise distort the data.

Thus there has been shown and described an improved motility scanner 10 and method designed for characterizing the motion of sperm, bacteria, particles suspended in flowing fluids, Brownian motion and the like, which scanner 10 and method satisfy the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. In a motility scanner of the kind for characterizing the motion of sperm, bacteria, particles in flowing fluids and the like, and comprising:

(a) an optical system including an imaging lens;

(b) a source of illumination for said system;

(c) a specimen support including a specimen holder disposed in the object plane of said imaging lens;

(d) radiation sensing means coupled to said system at the imaging plane of said imaging lens;

(e) signal processing means for analyzing signals generated by said radiation sensing means; and (f) display means coupled to said signal processing means for displaying information characteristic of said motion;

the improvement comprising said source of illumination including a single LED and a small source aperture designed to direct all of the illumination emanating from said source onto said specimen holder, and a movable plate designed to be swung into the beam of said imaging lens at a plane conjugate to the plane of said small source aperture, said plate provided with a centrally disposed retarding member and/or an attenuating member, with a part of said beam focussed by said imaging lens onto said retarding and/or attenuating member and with the remainder of said beam being focussed onto said plate surrounding said retarding and/or attenuating member, said single LED being one of high intensity, the improvement further including an electronic image reversal means forming a component part of said signal processing means, and switching means coupled to said electronic image reversal means for actuating the same.

2. In the motility scanner of claim 1 wherein the diameter of said centrally disposed retarding and/or attenuating member equals the diameter of said small source aperture multiplied by the magnification ratio of said optical system, and further including means for rotatably moving said movable plate from one operative position in the beam of said imaging lens to a second operative position outside said beam thereof.

3. In the motility scanner of claim 1 wherein said movable plate is made from glass and having a diameter of about 25 mm and a thickness of about 3 mm, and wherein said centrally disposed retarding member is formed of one of a group consisting of magnesium fluoride and titanium dioxide, and with a thickness of 120 nanometers and a diameter of about 0.115 inch.

4. In the motility scanner of claim 1 wherein said centrally disposed attenuating member comprises an absorbing layer formed of a nickel-base alloy characterized by high temperature oxidation resistance, and wherein said absorbing layer effects about 97% attenuation of that part of said imaging lens beam which is focussed thereon.

5. In the motility scanner of claim 3 wherein said centrally disposed retarding and attenuating members are coated on said movable plate, wherein said coating of said centrally disposed retarding and attenuating members is effected by evaporation onto said glass plate, and wherein said evaporation of said glass plate is effected via a mask designed both to mask said glass plate and to hold it in place during said evaporation process.

6. In the motility scanner of claim 5 wherein said retarding member is evaporated onto said glass plate first and said attenuating member is evaporated onto said retarding member.

7. In the motility scanner of claim 1 wherein the operative use of said movable plate in conjunction with said electronic image reversal means endows said motility scanner to be employed in one of three operative modes: (a) with bright field illumination; (b) with dark field illumination; and (c) with phase contrast illumination, and wherein said small source aperture has a diameter of about 0.04 inch and wherein said magnification ratio of said optical system is about 2.875.

8. In the motility scanner of claim 1 wherein said optical system further includes at least one reflecting element disposed between said single LED and small source aperture and said imaging lens.

* * * * *